US009119643B2

(12) United States Patent
Winslow et al.

(10) Patent No.: US 9,119,643 B2
(45) Date of Patent: Sep. 1, 2015

(54) METHOD AND APPARATUS FOR PERFORMING A LESS INVASIVE SHOULDER PROCEDURE

(71) Applicant: Biomet Manufacturing, LLC, Warsaw, IN (US)

(72) Inventors: Nathan A. Winslow, Warsaw, IN (US); Paul E. Schwartz, Palo Cedro, CA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 311 days.

(21) Appl. No.: 13/707,636

(22) Filed: Dec. 7, 2012

(65) Prior Publication Data

US 2013/0096564 A1 Apr. 18, 2013

Related U.S. Application Data

(62) Division of application No. 11/096,202, filed on Mar. 31, 2005, now abandoned.

(51) Int. Cl.
*A61B 17/15* (2006.01)
*A61B 17/17* (2006.01)

(52) U.S. Cl.
CPC ............. *A61B 17/1739* (2013.01); *A61B 17/15* (2013.01); *A61B 2017/1778* (2013.01)

(58) Field of Classification Search
CPC .............................. A61B 17/15; A61B 17/155
USPC ...................................................... 606/87, 89
See application file for complete search history.

(56) References Cited

U.S. PATENT DOCUMENTS

| | | | | |
|---|---|---|---|---|
| 5,108,396 | A * | 4/1992 | Lackey et al. | 606/62 |
| 2001/0047210 | A1* | 11/2001 | Wolf | 623/19.14 |
| 2003/0114859 | A1* | 6/2003 | Grusin et al. | 606/87 |

* cited by examiner

*Primary Examiner* — Nicholas Woodall
(74) *Attorney, Agent, or Firm* — Schwegman Lundberg & Woessner, P.A.

(57) ABSTRACT

A method and apparatus of performing a procedure relative to the glenohumeral joint. Resection of the glenoid and/or the humerus can proceed through an incision formed near the glenohumeral joint. The incision can be formed generally near a superior-lateral portion near the glenohumeral joint and allow less invasive access to the glenohumeral joint and the portions that form the glenohumeral joint. The procedure can be performed with no or little detaching of the subscapularis, and with no or little dislocating of the glenohumeral joint.

20 Claims, 13 Drawing Sheets

METHOD AND APPARATUS FOR PERFORMING A LESS INVASIVE SHOULDER PROCEDURE

CROSS REFERENCE TO RELATED APPLICATIONS

This application is a divisional application of U.S. application Ser. No. 11/096,202 filed on Mar. 31, 2005. The disclosure of the above application is incorporated herein by reference.

FIELD

The teachings herein are directed toward an orthopedic procedure, and particularly to a less invasive orthopedic procedure relating to the shoulder.

BACKGROUND

An anatomy, such as a human anatomy, includes various articulations, soft tissues, and hard tissues to perform various functions. Generally, these functions are carried out pain-free and with a substantial range of motion. Nevertheless, various functions may deteriorate over time as soft tissue or hard tissue deteriorates and articulations deteriorate. At a selected time, various portions of the anatomy may be replaced with artificial portions to restore substantially normal or anatomical motion and functionality.

For example, the articulation of the humerus with the glenoid (the glenohumeral or shoulder joint) may deteriorate. The humeral head or the glenoid may deteriorate and become rough or lose their anatomical shapes and reduce motion, increase pain, or the like. This may happen for various reasons, such as injury, disease, or lack of motion. This may lead to replacement of the selected portions of the anatomy with a prosthesis to achieve a substantially normal or anatomical range of motion.

Although it is known to replace various portions of the anatomy, such as a humeral head and a glenoid, many procedures generally require large incisions through soft tissue. Further, various procedures require that many muscle and muscle attachments be cut to achieve access to selected portions of the anatomy. Although it may be selected or necessary to perform many procedures in this manner, it may also be desirable to achieve a less invasive procedure.

Further areas of applicability of the present teachings will become apparent from the description provided hereinafter. It should be understood that the description and various examples, while indicating various embodiments, are intended for purposes of illustration only and are not intended to limit the scope of the teachings.

SUMMARY

A less invasive or minimally invasive procedure to achieve access to the articulation region, and the capsule surrounding the humeral head and the glenoid, to allow for replacement of at least one of the glenoid or the humeral head. The procedure can be performed by accessing the rotator cuff capsule by an incision near the shoulder and separating various muscle bundles and then incising the capsule. The procedure may be performed without substantial removal or resection of the subscapularis muscle or its attachment near the glenohumeral joint. Also other muscles forming the rotator cuff can remain intact as well. The procedure can allow for access to the rotator interval without a substantial dislocation or with no dislocation of the humeral head from the glenoid during the procedure.

According to various embodiments a method of performing an arthroplasty on at least one of a glenoid or a humeral head of a humerus through soft tissue of an anatomy is disclosed. According to various embodiments of the method an incision is formed in the soft tissue near a superior-lateral portion of the glenohumeral joint and portions the deltoid muscle are separated substantially superior and lateral of the glenohumeral joint. The humeral head can be resected and a prosthetic humeral head can be positioned to replace the resected humeral head. Also, the glenoid can be prepared and a glenoid implant can be inserted into the prepared glenoid. The separated muscle tissue and the incision in the soft tissue can be closed. The rotator cuff muscles, including the subscapularis muscle can remain substantially or completely connected during the arthroplasty procedure.

According to various embodiments a retractor to hold portions of an incision through soft tissue formed in an anatomy is disclosed. The retractor can includes a separation member extending between a first end and a second end. A second member can extend from near one of the first end or the second end of the separation member and a third member can extend from near one of the other of the first end or the second end of the separation member. A first spreading member can extend from the second member and a second spreading member can extend from the third member. A connecting member can be interconnected with one of the second member or the third member. The connecting member can allow selected movement of at least one of the first spreading member or the second spreading member relative to the other of the first spreading member or the second spreading member.

According to various embodiments, a glenoid protection device to protect a portion of the glenoid in an anatomy is disclosed. The glenoid protection device can include a graspable portion operable to extend through an opening in the anatomy. Extending from the graspable portion can be a shield member. The shield member is can be positioned near the glenoid when a portion of the anatomy is resected.

According to various embodiments, a humeral head resection guide is disclosed. The resection guide can includes a resection member defining a guide surface. Also, a first positioning member can be interconnected with the resection guide member and a second positioning member can be interconnected with the first positioning member.

According to various embodiments a glenoid resection guide for guiding the formation of various resections of a glenoid when performing a procedure relative to the glenoid is disclosed. The guide can include a member defining a perimeter including a top portion and a bottom portion and a bore defined by the member operable to guide a resection instrument to form a bore in the glenoid. A connection portion can be positioned at a top of the member. A handle can interconnect with the connection portion to assist in positioning the member relative to the glenoid. A user can grasp the handle and hold the handle during a resection procedure.

Further, various instruments are provided that allow for ease of accessing the anatomical portions and performing the less invasive procedure. For example, cutting guides, according to various embodiments, can be provided that interconnect with selected portions, such as reamer bodies, for positioning the cutting guide to perform a procedure. Further, various retractors, reamers, and the like can be provided to achieve a selected result.

BRIEF DESCRIPTION OF THE DRAWINGS

The present teachings will become more fully understood from the description and the accompanying drawings, wherein.

DETAILED DESCRIPTION OF VARIOUS EMBODIMENTS

Figure 1:
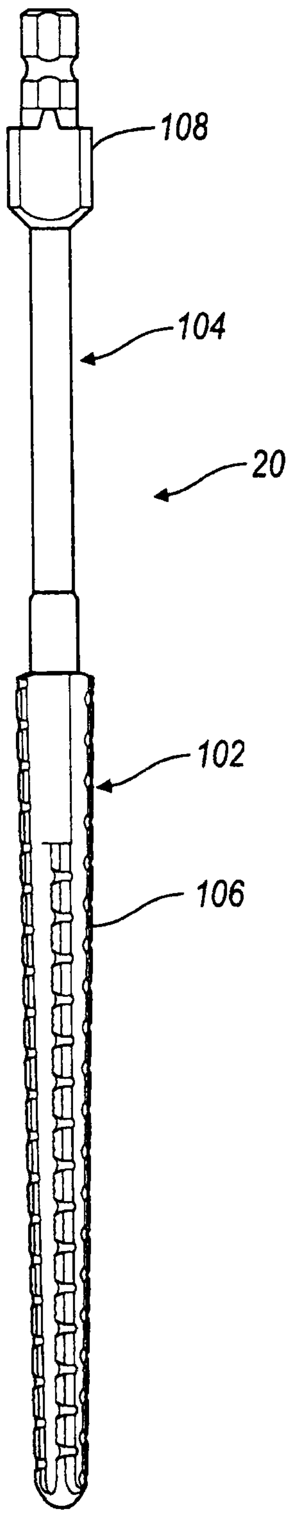
FIG. 1 is an elevational view of a reamer according to various embodiments.

The following description of various embodiments is merely exemplary in nature and is in no way intended to limit the teachings herein, its application, or uses. Although the following description is discussed specifically for performing a procedure of a shoulder of the human anatomy, it will understood that the procedure and instruments described herein may be augmented and used for various other procedures or in other anatomies. Therefore, although the following description is related to a shoulder procedure, it will be understood that the teachings herein are not so limited.

Various instruments can be used in performing a selected procedure, such as a shoulder arthoplasty. It will be understood that various instruments and procedures may be used to perform a hemi-arthoplasty, such as replacement of only one of a humeral head or a glenoid. A total arthoplasty can be the replacement of a humeral head and a glenoid where the humeral head and the glenoid can articulate with one another after implantation. Nevertheless, instruments can generally include a reamer 20 (FIG. 1), a drill motor 30 (FIG. 2), a resection shield 40 (FIG. 3), an inserter/broach instrument 50 (FIG. 4), a retractor 60 (FIGS. 5A and 5B), a resection guide 70 (FIGS. 6A and 6B), a glenoid guide 80 (7A and 7B), a resection saw and motor 90 (FIG. 8) and a glenoid reamer 100 (FIG. 9). It will be understood that various other instruments may be provided for using or performing a selected procedure and the described instruments are merely exemplary. Nevertheless, the instruments taught herein can be used to achieve selected results in a selected procedure.

With reference to FIG. 1, the reamer 20 can include a reaming body 102 and a drive shaft 104. The reaming body 102 can include a plurality of cutting sections 106 and may be formed in any selected manner. As discussed herein, the reamer 20 may be used to ream a selected portion of the anatomy such as a humerus, and may, therefore, include an extended body including the cutting sections 106 extending along the extended body 102. The reamer 20 may ream an intramedullary (IM) canal of a selected bone, such as the humerus.

Figure 2:
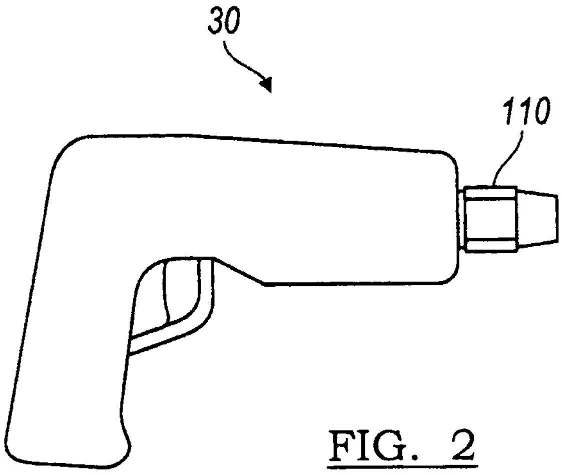
FIG. 2 is an elevational view of a drill motor according to various embodiments.

The reamer shaft 104 may include a quick connect section 108 that can interconnect with a selected portion, such as a chuck 110 of the drill motor 30 (FIG. 2). The drill motor 30 may be any appropriate drill motor such as those generally known in the art. Nevertheless, the drill motor 30 may be electrically powered, hydraulic powered, or use any appropriate power source. It will be understood that the chuck 110 of the drill motor 30 may interconnect with the reamer 20 in any appropriate manner and the quick connect 108 is merely exemplary. Regardless, the quick connect 108 may allow for a quick and efficient procedure and may allow for easy connection and disconnection of the reamer 20 from the drill motor 30 so that the drill motor 30 may be used for other instruments. Also the reamer 20 need not be powered or driven with a motor. The reamer 20 can be manually driven into a bone, such as with impaction or twisting.

With any appropriate power, the reamer 20 can be used to ream a selected portion of the anatomy and various instruments can be interconnected with the reamer 20, as discussed herein. It will be understood that the instruments may be interconnected with any appropriate portion of the reamer 20 such as the shaft 104 or the quick connect 108.

Figure 3B:
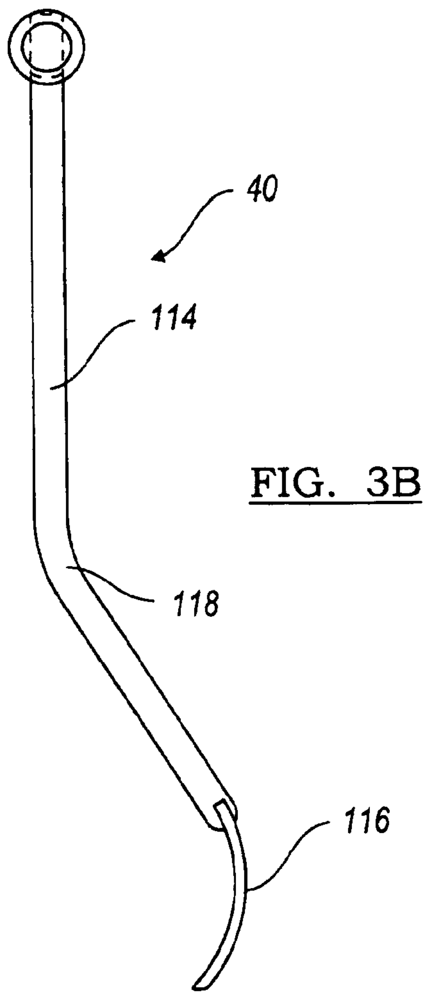
FIG. 3B is a side elevational view of a resection guard of FIG. 3A.
Figure 3A:
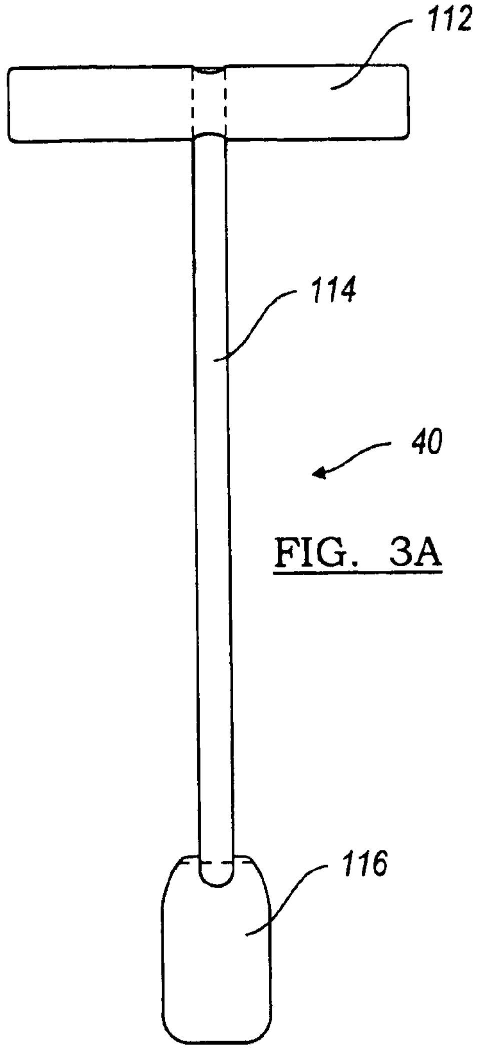
FIG. 3A is a front elevational view of a resection guard according to various embodiments.

With reference to FIG. 3, the resection or glenoid protector 40 can be used in a procedure for protecting various portions of an anatomy that are selected to be engaged with an instrument at a selected time. The resection protector 40 may include a handle 112 that is connected through a shaft 114 to a protector or protective paddle 116. The protective paddle 116 can include any appropriate profile, such as a substantially curved profile that may rest on an unresected or resected glenoid. The protective shield 116 can engage a portion of a glenoid 314 (FIG. 13) to protect the glenoid 314 when a humeral head 310*a* (FIG. 13) is being resected, as discussed herein. Therefore, the protective shield 116 can protect a selected portion of the anatomy from a resection procedure that is not intended to resect that selected portion of the anatomy.

The shaft 114 may include a selected geometry, such as a bent area 118 to assist in positioning the protective shield 116 in an appropriate position. The protective shield 116 may be formed of any appropriate material, and the material may generally be biocompatible. For example, the shield 16 may be formed of a metal, such as stainless steel or titanium, that can resist at least a short period of engagement with a cutting apparatus. Alternatively, or in addition thereto, the protective shield 116 may be formed of a polymer or other material. The handle 112 allows a user to hold the protective shield 116 in a selected position.

Figure 4:
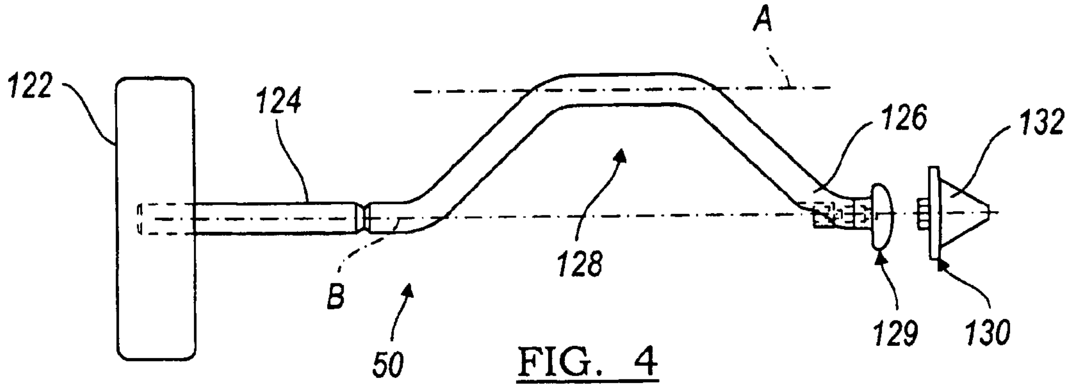
FIG. 4 is a side elevational view of a tool according to various embodiments.

With reference to FIG. 4, an instrument 50 may be comprised of various portions to assist in performing a selected procedure. The instrument 50 may include a handle 122 that is interconnected with a shaft 124 that includes a distal engagement region 126. The shaft 124 may also include a bent or unaligned portion 128. The unaligned portion 128 can include a portion that extends along an axis A that can be parallel, but displaced from an axis B that extends through another portion of the shaft 124. It will be understood that the axis A of the offset portion 128 may also be at any appropriate angle relative to the axis B and being substantially parallel is merely exemplary.

The engagement region 126 of the shaft 124 can be used to engage various elements. For example, the engagement end 126 can engage an inserter 129. The inserter 129 may be used to insert various portions, such as a glenoid implant, described herein. Alternatively, or in addition thereto, the engagement end 126 may engage a broach 130. The broach 130 may be used for broaching various portions of the anatomy, such as the glenoid 314, for receiving a glenoid implant. For example, the broach 130 may include a broaching portion 132 that can broach an area of the glenoid to receive a keel of a selected glenoid implant. It will be understood that various other portions may be engaged to the engagement end 126 of the tool 50 and the inserter 129 or the broach 130 are merely exemplary.

Further, the handle 122 can be used to be struck by a hammer or other appropriate instrument to assist in using the broach 130 or the implant inserter 129. Alternatively, the handle 122 may be simply pressed or pushed by a user to engage the selected portion of the anatomy with the portions engaged on the engagement end 126.

Figure 5A:
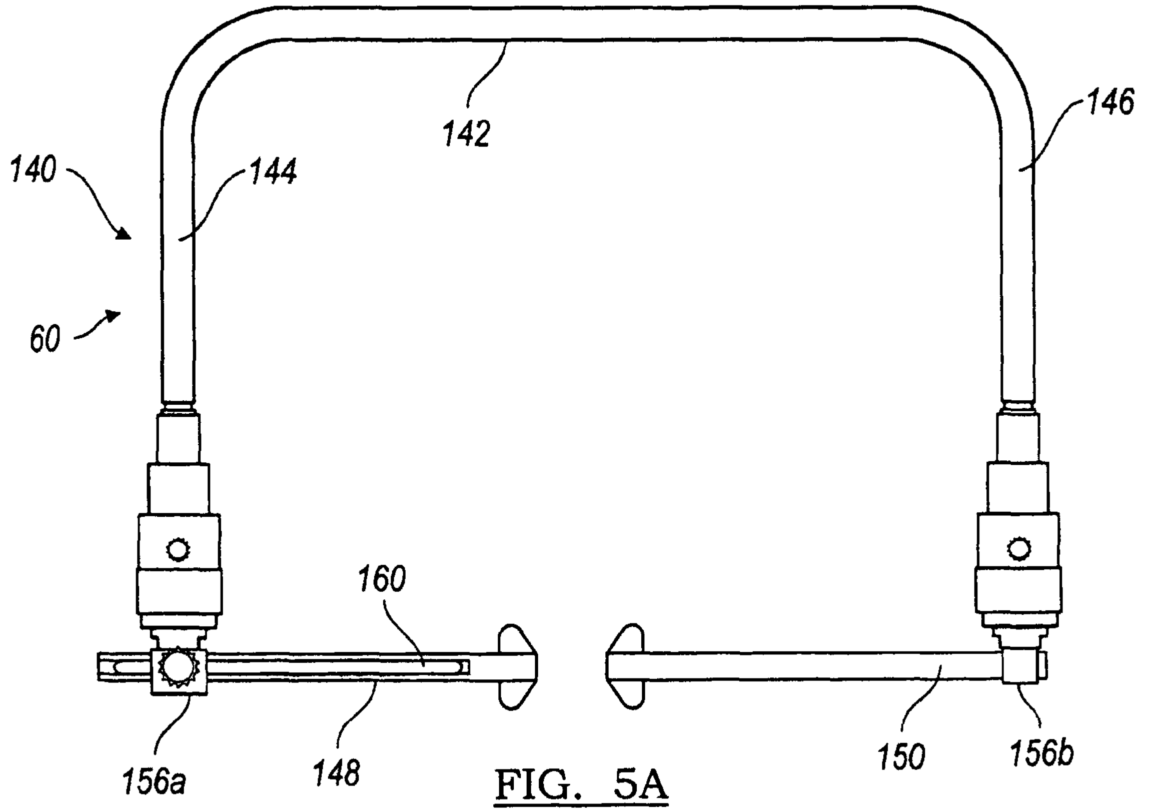
FIG. 5A is a top elevational view of a retractor according to various embodiments.
Figure 5B:
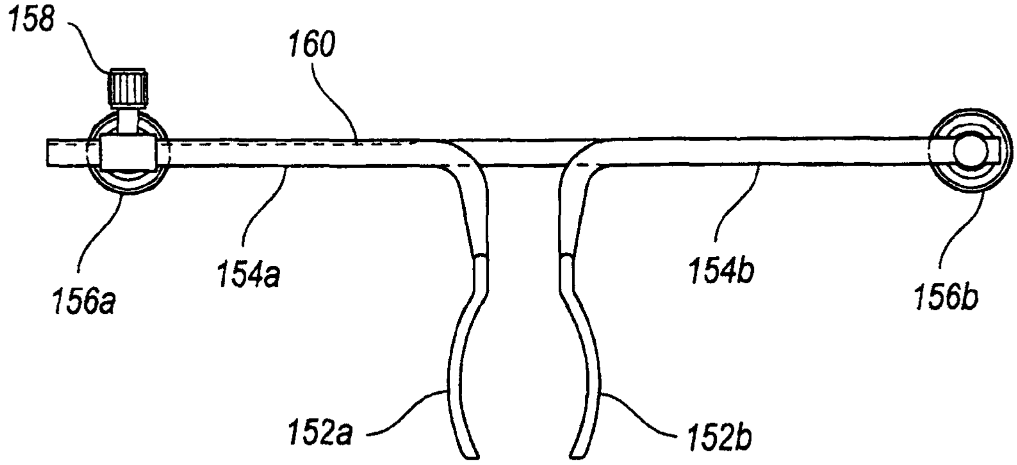
FIG. 5B is a front elevational view of a retractor of FIG. 5A.

With reference to FIGS. 5A and 5B, the retractor 60 may be used to retract or position a selected portion of the anatomy. As discussed herein, an incision 316 (FIG. 10) can be formed in selected soft tissue portions of an anatomy and the retractor 60 may be used to hold the edges of the incision apart or to spread the incisions apart to obtain access to a selected portion of the anatomy. The retractor 60 can also be used to retract or hold tissue that is deep within the incision. For example, the retractor 60 can be used to allow clear access to a selected anatomical position, such as a humeral head 310*a*. The retractor 60 can be used in any appropriate procedure, and its description for use in a shoulder procedure is merely exemplary.

The retractor 60 can include a retractor body 140 that is a substantially U-shaped or any other appropriate shape. The body 140 generally includes a spacing portion 142 that separates a first arm 144 from a second arm 146. The spacing portion 142 can define a selected distance between the arms 144, 146 to allow for positioning of a first retracting element 148 from a second retracting element 150. Although the retracting elements 148, 150 can be moved relative to the retractor body 140, the spacing portion 142 of the body 140 may assist in the initial positioning the retracting elements 148, 150.

The retracting elements 148, 150 may be substantially similar to each other. Alternatively, the retracting elements 148, 150 can be formed differently for various purposes. Nevertheless, retracting elements 148, 150 can generally include soft tissue engagement portions 152*a*, 152*b*. The soft tissue engagement portions 152*a*, 152*b* can be interconnected with retracting portions 154*a*, 154*b* respectively. The soft tissue engagement portions 152*a*,152*b* can be shaped to cooperate with a selected portion of the anatomy, such as the humeral head 310*a*.

The retracting portions 154*a*, 154*b* can be interconnected with retractor body 140 in any appropriate manner. For example, the retracting elements 148, 150 can be engaged in holding members 156*a*, 156*b*, respectively. Each of the holding members 156*a*, 156*b* can allow the retracting elements 148, 150, respectively, to move relative to the body 140. Alternatively, either one of the retracting elements 148, 150 can be fixed relative to the retractor body 140 while only the other one can move.

At least one of the connecting portions 156*a* or 156*b* can include a set or holding screw 158 that can be moved through a threaded portion in the holding section 156*a* to engage a track or portion 160 of the retracting element 148. The track 160 can be a flat or any appropriately shaped portion of the retracting element 148 that can be engaged with the set screw 158. In this way, the retracting element 148 can move relative to the connecting portion 156*a* and be held in the selected position with the set screw 158. It will be understood that the second connecting portion 156*b* may include a similar apparatus and the retracting element 150 may also include a similar geometry and only one is illustrated for discussion purposes.

The retractor 60 can be used to retract a selected portion of the anatomy to hold it in a selected position to allow access to various portions of the anatomy. It will be understood that various other retractors may be used for selected procedures and the retractor 60 is merely exemplary.

Figure 6A:
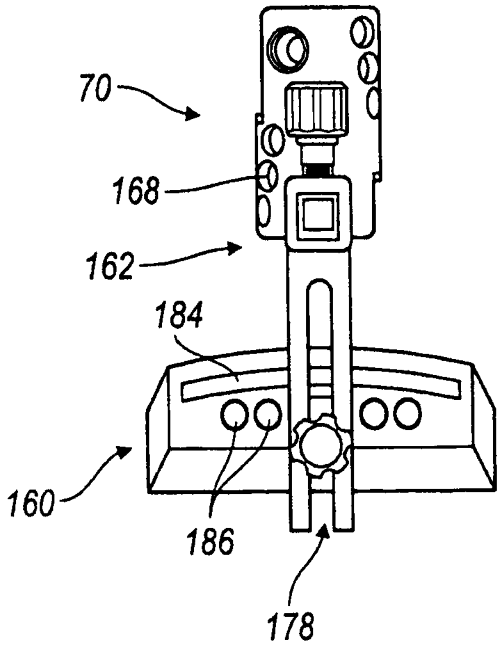
FIG. 6A is a front elevational view of a resection guide assembly according to various embodiments.
Figure 6B:
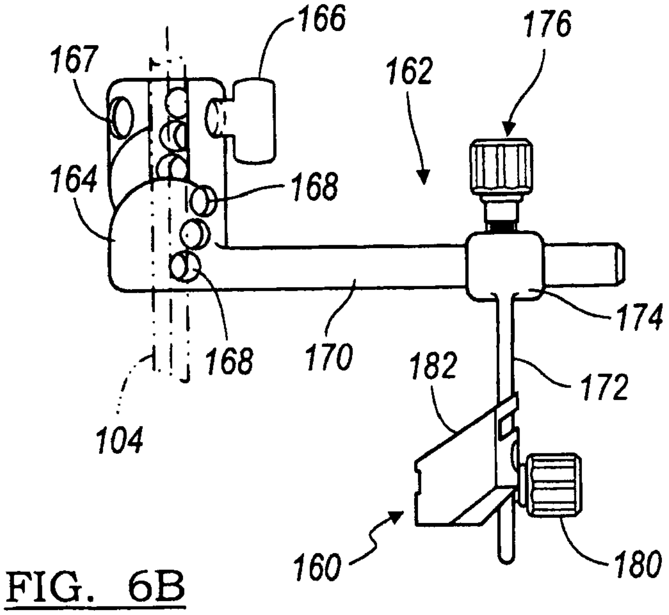
FIG. 6B is a side elevational view of a resection guide assembly of FIG. 6A.

With reference to FIGS. 6A-6B, a cutting guide 70 can be used to guide a cutting instrument, such as a saw blade, relative to a selected portion of the anatomy. The cutting guide 70 generally includes a guiding member 160 and an attachment portion 162. The attachment portion 162 includes a rod attachment portion 164 that can interconnect with a rod or any appropriate member, such as the shaft 104 (shown in phantom for illustration). A set screw or locking screw 166 can be provided to lock the mounting portion 162 relative to the shaft 104. It will be understood that any appropriate locking mechanism can be provided and that set screw 166 is merely exemplary.

The set screw 166, however, may be interconnected through any one of a plurality of bores 167 formed in the connection member 164. In this way, the engagement member 162 can be interconnected with the shaft 104 in a plurality of locations to achieve an appropriate or selected orientation. As discussed herein, the guide block 160 can be oriented relative to a selected portion of the anatomy, such as the humerus. The cutting block 70 can be interconnected with the shaft 104 in a plurality of positions that may assist in appropriately orientating the guiding block 160 relative to the portion of the anatomy. Also version bores 168 can, for example, be used for version rod control to select an angle for the resection. The version rod can be interconnected with one of the bores 168 depending upon a selected angle for the cutting guide 70. The various version bore 168 can relate to differing degrees of version.

It will be understood that the attaching portion 164 may also attach to a member, such as the shaft 104 in a plurality of manners. For example, the connecting member 164 may be interconnected with the shaft 104 using the quick connect portion 108 of the reamer 10. This can allow the connecting portion 162 to be efficiently and quickly interconnected with the reamer 10 according to various embodiments. Nevertheless, the set screw may also allow for easy and selectable orientation of the cutting guide 160 relative to a selected portion of the anatomy.

Extending from the attachment portion 164 is an arm 170 that interconnects with a second orientating arm 172. The second orientating arm 172 can include a connection region 174 that defines a bore through which the connection arm 170 may extend. A second set screw 176 can be provided to assist in holding the second orientation arm 172 relative to the arm 170 of the connection portion 162. Therefore, the orientating arm 172 can be moved relative to the connecting region 164 of the positioning member 162.

The orientating arm 172 can define a groove or track 178 in which a third set screw 180 can be moved. The third set screw 180 can interconnect the cutting guide 160 with the second orientating arm 172. This allows the cutting guide 160 to be moved relative to the first orientating member 162 in a plurality of orientations. Therefore, the cutting guide 160 can be moved in several degrees of freedom relative to the shaft 104, or any appropriate member, to achieve a selected orientation of the cutting guide 160 relative to a selected portion of the anatomy.

The guide member 160 can include or define a plurality of guide surfaces. For example, an exterior portion 182 of the guide member 160 can define a guide surface. Alternatively, or in addition thereto, a groove or slot 184 can be defined by the cutting guide that can also define a guide surface. It will be understood that the guide member 160 can include a plurality of guide surfaces and those illustrated are merely exemplary.

The guide member 160 can also define a plurality of fixation bores 186 that allow for fixation of the cutting guide 160 relative to a selected portion of the anatomy, such as discussed herein. Therefore, the apparatus 70 can assist in positioning and orientating the cutting guide 160 relative to a selected portion of the anatomy, such as a humerus, and various fixation members can be used to hold the cutting guide 160 relative to a selected portion of the anatomy during a resection process. It will be understood, however, that the apparatus 70 may also hold the cutting guide 160 relative to a selected portion of the anatomy during a resection process.

Figure 7B:
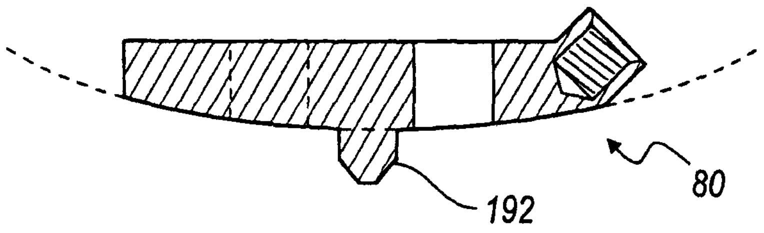
FIG. 7B is a side cross-section view of a resection guide of FIG. 7A.
Figure 7A:
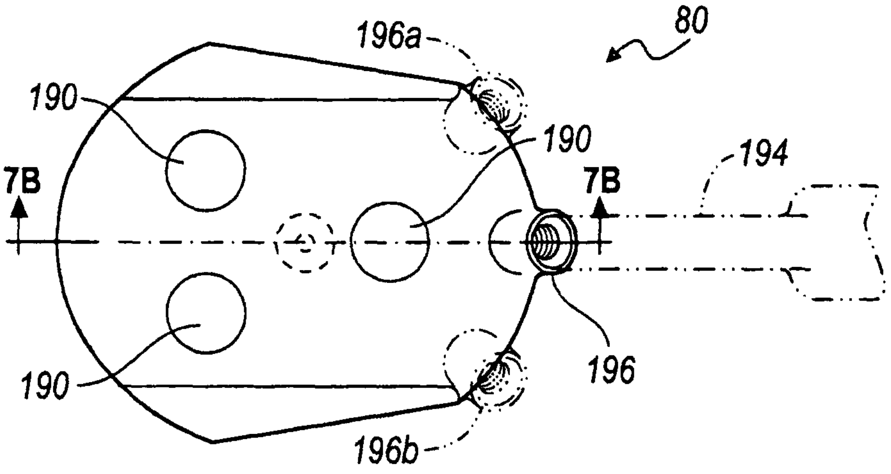
FIG. 7A is a top elevational view of a resection guide according to various embodiments.

With reference to FIGS. 7A and 7B, a glenoid guide 80 is illustrated. The glenoid guide 80 can be shaped and include a plurality of shapes and sizes for inclusion in a kit or system and an individual guide may be selected by a user, such as a physician, for a selected procedure. The various guides may include different guide portions, different guide bores, different sizes, different shapes, or other appropriate differences that may be chosen for a selected patient or use by a physician. The glenoid guide 80, however, generally includes a guide bore or channel 190. The glenoid guide 80 may also include a plurality of the bores 190 for forming a plurality of bores or tunnels in a selected portion of the anatomy, such as a glenoid. The glenoid guide 80 also generally includes a selected orientation or exterior geometry that can assist in determining appropriate fit of the guide 80 relative to the glenoid. A centering or positioning post 192 can extend from the glenoid guide 80. The post 192 can be positioned in a bore formed by an initial guide member, such as that generally known in the art. The projection 192 helps to assure an appropriate orientation of the guide 80 relative to the glenoid when forming the plurality of bores defined by the guide bores 190.

The glenoid guide 80 is generally held in a selected position by a user with a positioning arm 194 or tool that is interconnected with the glenoid guide 80 at a connection region 196. The connection region 196 can be positioned generally along a central axis C defined by the glenoid guide 80. The positioning of the attachment region 196 along the axis C can allow for ease of use by a user and allow for a plurality of orientations of the guide 80 relative to a selected portion of the anatomy. It will be understood that the connection region 196 may also be positioned in other orientations on the glenoid guide. For example, the attachment region 196 can be positioned at a top and first side of the glenoid guide 80 to form a first alternative connection region 196*a*. Alternatively, or in addition thereto, a second attachment portion 196*b* can be provided on a second side of the glenoid guide 80. Therefore, the glenoid guides 80 can be substantially size specific or can be universal where a user may move the holding member 194 between the various connection regions 196 to achieve a selected orientation of the handle 194 for ease of use by a user.

Figure 8:
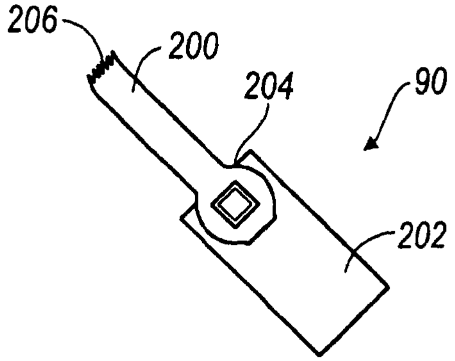
FIG. 8 is a perspective view of a saw and saw motor according to various embodiments.
Figure 9:
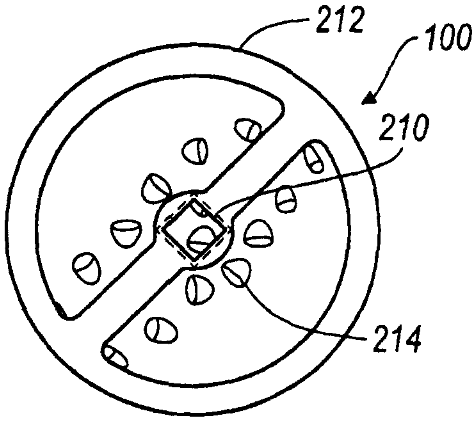
FIG. 9 is a top elevational view of a reamer according to various embodiments.

With reference to FIG. 8, the resection instrument 90 can be any appropriate resection instrument. For example, the resection instrument 90 can be a resection saw generally known in the art. The resection saw 90 can include a saw blade 200 that is operated by a saw motor 202. The saw blade 200 can include a motor attachment region 204 and a tooth or cutting region 206. The saw blade 200 can be used with the guide member 160 to resect a selected portion of the anatomy, as described herein. It will be understood, however, that any appropriate resection instrument may be used to achieve a selected result and the resection saw 90 is merely exemplary.

With reference to FIG. 9, the reamer 100 can be used to ream a selected portion of the anatomy, such as a glenoid. The reamer 100 can be used to ream the glenoid, such as that described herein, to achieve an appropriate position of a glenoid implant or to expose bone that is strong enough to support a glenoid implant. The reamer 100 can be any appropriate reamer, such as those generally known in the art, that include a tool attachment 210, a rim 212, and cutting edges 214. The tool attachment region 210 can interconnect with any appropriate tool, such as a manual tool or a power tool. The reamer 100 can be powered with any appropriate motor, such as the drill motor 30. The reamer 100, however, can be used to ream a selected portion of the anatomy, such as the glenoid, to allow for positioning of an implant.

All of the instruments described above are exemplary. They can be used in a plurality of procedures to assist a user in an orthopedic procedure. For example, the instruments described above can be used to assist in resecting a selected portion of a humerus and a glenoid to allow for implantation of a shoulder implant, including a humeral implant and a glenoid implant. Described below and illustrated in FIGS. 10-16 is a procedure performed relative to a human anatomy 300. It will be understood that the following method is merely exemplary and is not intended to limit the scope of the above-described instruments. Similarly, the procedure herein is exemplary of a procedure that may be performed relative to a selected portion of the anatomy and, although a shoulder procedure is described, it is not intended to limit the teachings herein.

Figure 10:
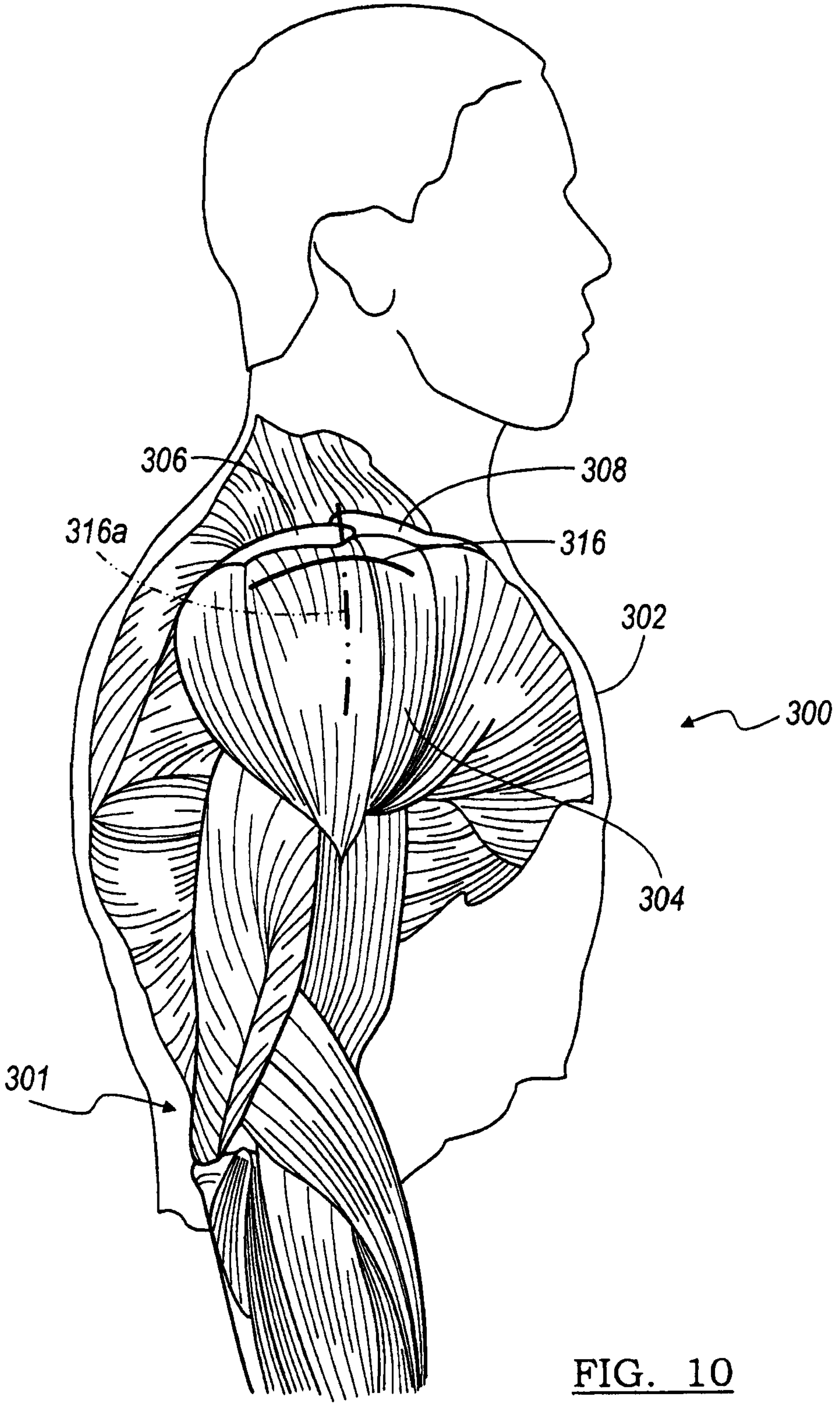
FIG. 10 is a side elevational view of an anatomy.
Figure 11:
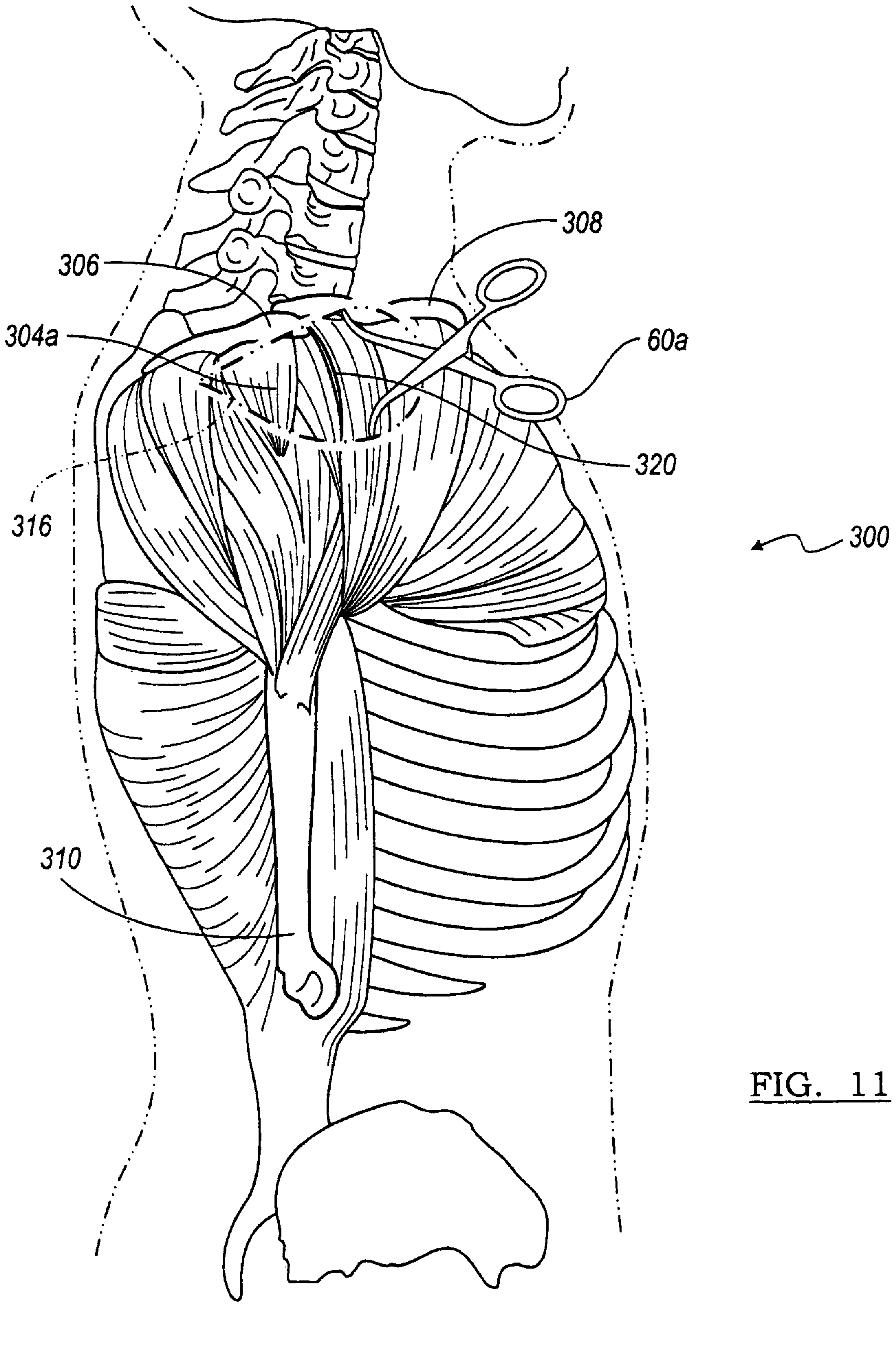
FIG. 11 is a side elevational view of an anatomy including an incision according to various embodiments.
Figure 12:
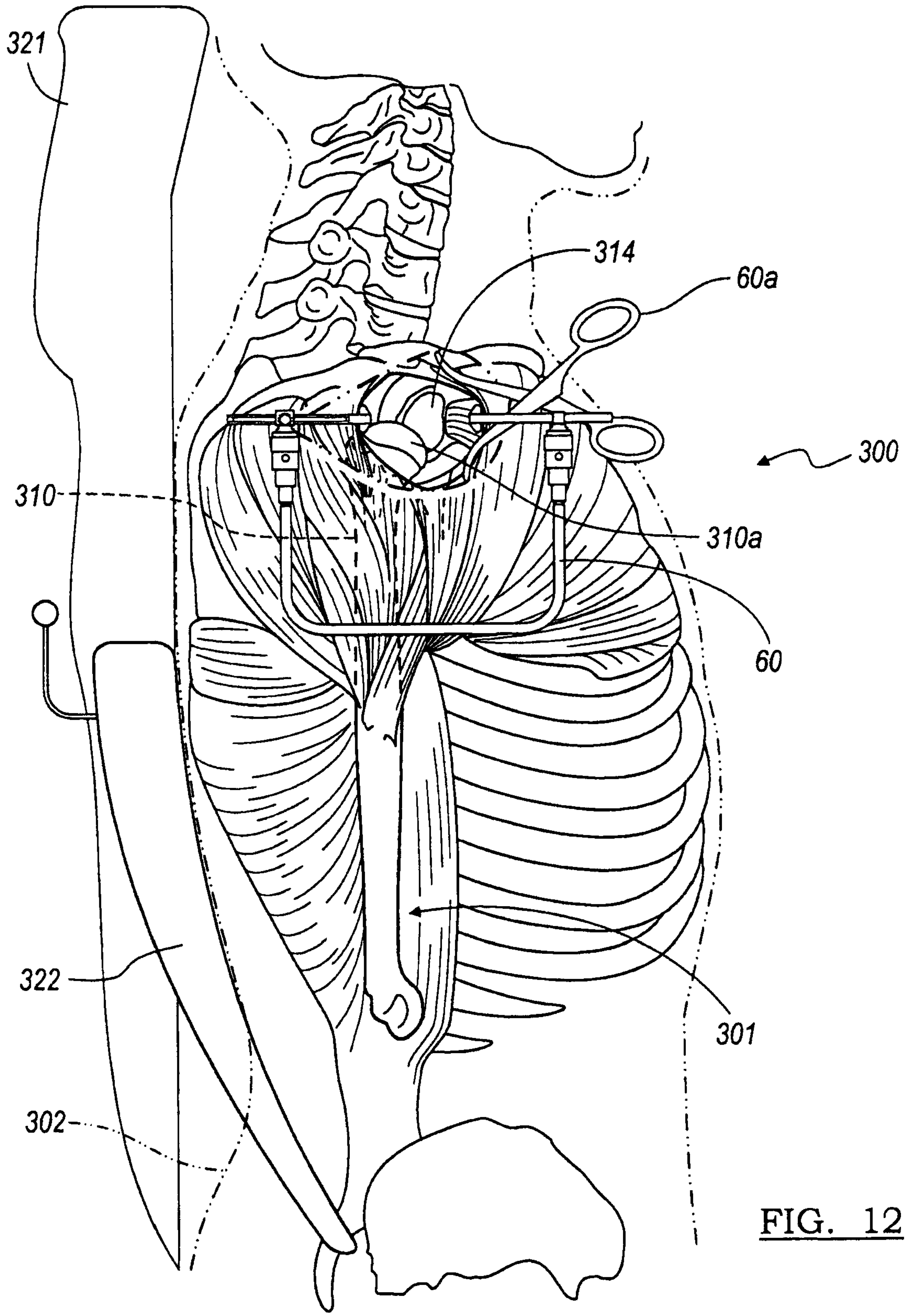
FIG. 12 is a side elevational view of an anatomy including an incision and exposure of anatomical portions according to various embodiments.

With initial reference to FIG. 10, a human anatomy 300 can be augmented with the use of the instruments illustrated in FIGS. 1-9. The human anatomy 300 generally includes an external skin layer 302 and soft tissue there below, such as muscle 304. Below the soft tissue, and the soft tissue may be interconnected therewith, includes bony portions such as an acromion 306, a clavicle 308, a humerus 310, and a scapula 312, which can define a glenoid 314. Various portions of the anatomy, including the humerus 310 and the glenoid 314, can be accessed by forming an incision 316 in the soft tissue, including the skin 302.

Also, various subdermal portions, such as subdermal adipose tissue, can be incised along the incision 316. It will be understood that the incision 316 can be orientated in any appropriate direction such as anterior to posterior, which is generally parallel to a sagittal plane. Alternatively, or in addition thereto, a superior-inferior incision illustrated in phantom 316*a*, which is generally along the coronal plane, can be made. The skin incision can made parallel with Langerhan's lines at the superior aspect of the shoulder, just even with the lateral border of the acromion 306. The incision 316 can also be medialized slightly. The incision 316 can be any appropriate length, and may depend upon surgeon preference, patient type, prosthetics to be used, or other indications. Nevertheless the incision can be about 3 cm (about 1 in) to about 20 cm (8 in) in length such as about 7.5 cm (about 3 in) to about 10 cm (4 in). It will be understood that the incision 316 through the skin may be shorter than the area opened in the muscle 304. The incision 316 can be used to achieve access to the muscle 304 that is around the various portions of the anatomy that are selected to be resected, including the humerus 310 and the glenoid 314. The incision can be used to obtain access to a deltoid muscle 304*a*.

The retractor 60*a* can be any appropriate retractor such as a Gelpi Style Retractor. It will be understood that the retractor 60 may also be used to retract the soft tissue, such as the muscles surrounding the glenohumeral joint, including the deltoid muscle 304*a*, but the Gelpi Style Retractor may also be used to expand the incision 316 to gain access to the muscle. The retractor 60, as illustrated herein, can be used to retract or position the deep tissue that is generally near the glenohumeral joints.

Through the incision 316, which can be expanded with the Gelpi Style Retractor 60*a*, the deltoid muscle 304*a* can be seen. The deltoid muscle 304*a* can include various muscle fibers and bundles that interconnect the humerus 310 with other portions of the anatomy, such as the clavicle 308 or the acromion 306. A muscular split or incision 320 can be formed between the various fibers of the deltoid muscle to obtain deeper access into the anatomy 300. The separation 320 can be a passage formed through the cuff internal of subscapularis and the supraspinatus. It will be understood that the separation 320 in the muscle can be formed in any appropriate manner according to various selected methods and preferences of a physician. Nevertheless, the separation 320 can be made to separate various muscle fiber bundles to allow for ease of access to the muscle regions. The deltoid 304*a* can be split in line with its fibers along the anterior border of the acromion 306, and laterally along the raphe between anterior and middle thirds of the deltoid. Laterally, the split 320 can go as far as about 7 cm, with care taken to avoid the axillary nerve, and medially can be taken along the anterior aspect of the distal clavicle, medial to the acromion/clavicle (A/C) joint. An incision can be formed from the distal clavicle about ½ cm medial to the A/C joint, out to about 4 cm past the lateral border of the acromion 306. A Gelpi retractor 60*a* or the retractor 60 can be placed to open the interval.

The passage 320 through the deltoid 304*a* can achieve access to various deeper soft tissue portions, such as the sub-deltoid bursa and the subacromial bursa. Further, various other deep soft tissue can be incised and/or moved to achieve access to the capsule surrounding the shoulder or glenohumeral joint. After moving and/or incising all of these portions, access to the humerus 310 or the humeral head 310*a* can be achieved.

The retractor 60 can be used to hold the various soft tissues portions open, such as the cuff interval, capsule and the like. It will be understood that the retractor 60 may be any appropriate retractor and may include a scissor retractor or the like. Various other soft tissue portions may be near the capsule and may also be incised or resected. For example, the bicep tendon that interconnects to a portion or near the humeral head 310*a* may be resected or may be moved, if already detached, to achieve better access to the humeral head 310*a*. Further, access to the glenoid 314 can also be seen once the soft tissue has been incised.

Although the incision 316 on the shoulder or near the glenohumeral joint allows access to the deltoid muscle 304*a* and access to the capsule and soft tissue surrounding the glenohumeral joints, various muscles and ligaments need not be resected or incised when obtaining access to the glenohumeral joint according to the process discussed herein. For example, the subscapularis muscle and the ligaments attaching it to the portions of the glenohumeral joint need not be incised when obtaining access to the glenohumeral joint according to embodiments of the teachings herein. The subscapularis muscle can be left intact because it is generally anterior from the approach described. Also the supraspinatus can remain intact, as may all the muscles of the rotator cuff. Rather the passage 320 can be formed by separating the cuff interval rather than detaching or incising various soft tissue portions. Further, the humeral head 310*a* need not be substantially dislocated or dislocated at all from the glenohumeral joint according to various embodiments. Rather, the humeral head 310*a* can be moved to allow access to various portions of the anatomy, however, major dislocation of the humeral head 310*a* from the glenoid 314 is not necessary. The humerus can be left in its generally anatomical position or retracted any appropriate distance, such as about 2 cm to about 8 cm.

If the rotator cuff is intact, but there is significant prominence of the anterior acromion 306, a routine acromioplasty is performed at this stage. If significant A/C joint arthritis is present, a distal clavicle resection is commonly performed. This relieves pain from the arthritis, and further opens the exposure to the glenohumeral joint. If the cuff is torn, but appears repairable, an acromioplasty is similarly performed, and a cuff repair is accomplished upon completion of the arthroplasty. If, on the other hand, there is a massive, irreparable cuff lesion, then an acromioplasty may not be performed, and the coracoacromial ligament is preserved, and repaired along with the deltoid at the end of the procedure.

The lesser tuberosity and the bicepital groove are palpated, and the rotator interval over the top of the biceps tendon is incised. The cuff incision follows over the top of the biceps along the anterior border of the supraspinatus as far medially as can be exposed. The biceps tendon is then detached from the superior labrum and tagged for later tenodesis.

The soft tissue over the biceps laterally is sharply dissected off the humerus down to the top of the subscapularis tendon, but the tendon can be left undisturbed. The supraspinatus may be stripped back off the anterior portion of the greater tuberosity for a distance of about 5 mm to about 10 mm to further enhance the exposure. More than 1 cm may not be detached, and the basic integrity of the tendon can remain. This exposure of the rotator interval typically gives about a 1.5 cm to about 2 cm gap at the lateral edge, without disrupting the rotator cuff mechanism. The Gelpi retractor 60*a* can be moved from the deltoid 304*a* to the rotator interval and this can provide greater exposure of the glenohumeral joint for instrumentation and implants.

Further, the person or the anatomy 300 can be positioned on an operating table or bed 321. An arm 301 of the anatomy 300 can be positioned on the positioning board 322 that can be interconnected with the bed 321. This can assist in holding the arm 301 in a selected position to obtain a desired orientation of the glenohumeral joint. Further, the arm 301, including the humerus 310, can be moved in a selected orientation to assist in achieving a selected access to the glenohumeral joint or various portions of the anatomy, such as the humeral head 310*a* and the glenoid 314.

Once access to the humeral head 310*a* and/or the glenoid 314 has been achieved, various resection procedures can occur. Although the muscles have been incised to obtain access to the glenular humeral joint, various muscular portions, such as the subscapularis muscle, may not have been incised or disconnected from the various boney portions. Therefore, the instruments, such as those described above, can be used to assist in achieving a selected resection of the anatomy through the incision made and allowing various portions of the muscle to remain intact.

Figure 13:
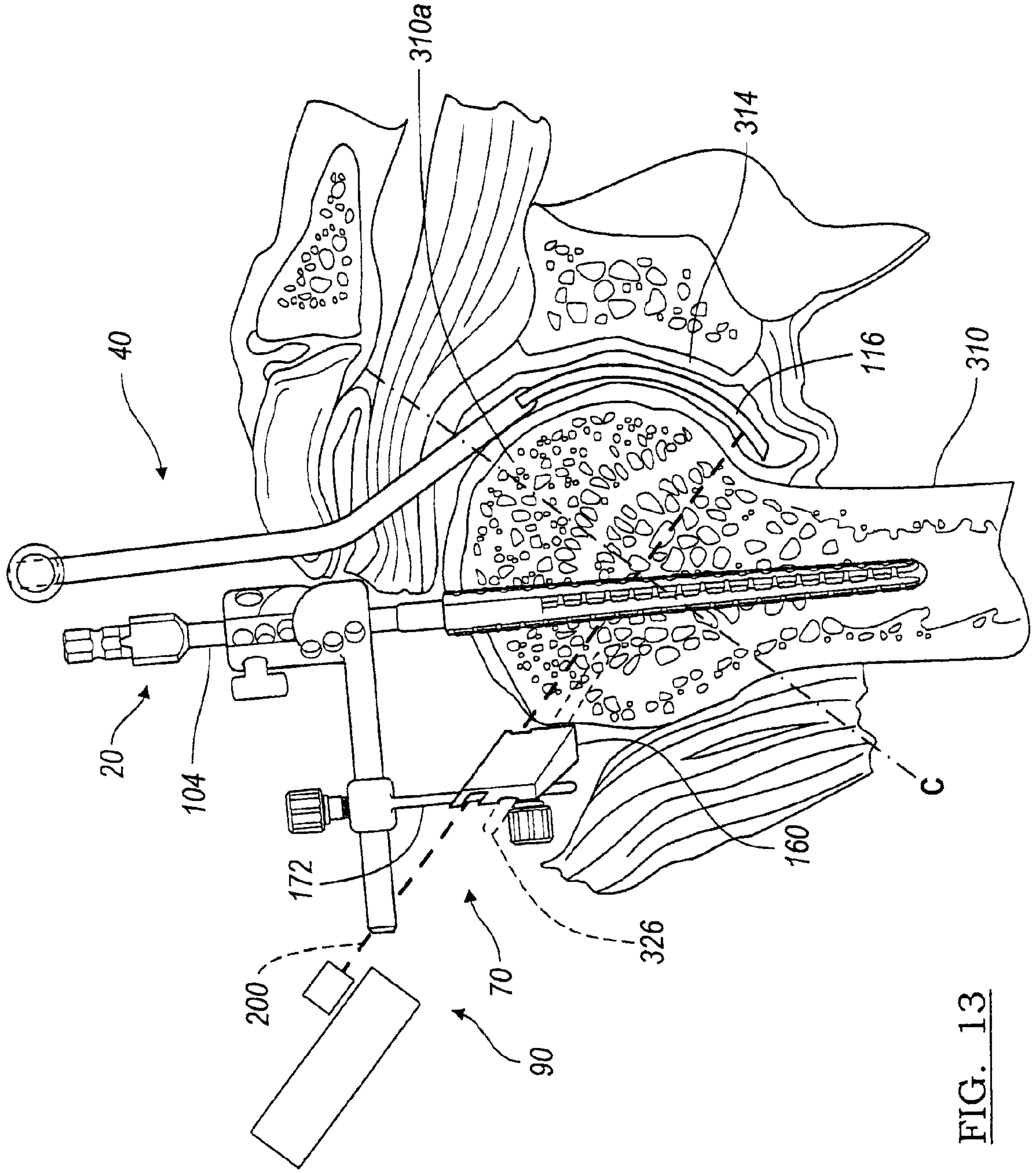
FIG. 13 is a detail cross-section view of an anatomy including an incision and positioning of various instruments according to various embodiments.

Once access has been obtained to the glenohumeral joint, various instruments according to various embodiments can be used in the procedure. It will be understood that according to various embodiments, any, all, or none of the instruments may be used in a procedure. With reference to FIG. 13 (detailed view of the glenohumeral joint), the reamer 20 can be reamed into the humerus 310 near the humeral head 310*a*. Humeral reaming can occur from the superior, lateral humeral head. The entrance to the head 310*a* can be just underneath the previous location (i.e. the natural location) of the biceps tendon. The arm 301 can be extended slightly, and the elbow can be placed against the patient's side to bring the top of the humeral head 310*a* forward, and allow the reamer to pass the front of the acromion 306. This can allow the humeral head 310*a* to be retracted, but remain substantially or completely undislocated. This can reduce trauma in the surrounding soft tissue. The superior approach allows easy centering of the reamer in the humeral head and proximal shaft, and decrease the initial incidence of varus stem placement and/or eccentric head utilization.

The reamer 20 includes the shaft 104 that can extend from the humerus 310. The reamer 20 can be positioned into the humerus and interconnected with various portions, such as the guide apparatus 70. The guide apparatus 70 can be interconnected with the shaft 104 of the reamer 20 while the reamer remains in the humerus 310. This allows for positioning the cutting guide 160 relative to the humerus 310 and the humeral head 310*a*.

As discussed above, the various portions of the apparatus 70, including the guide movement arm 172, can be used to orient the cutting guide 160 in a proper orientation relative to the humeral head 310*a*. Generally, it is selected to obtain or position an axis of the cutting guide 160, such as a central axis, relatively in line with the humerus 310. This can help position the guide surface, along which the saw blade 200 (shown in phantom in FIG. 13) can be guided), generally perpendicular to an axis C of the humeral head 310*a*.

The cutting guide 70 can generally be positioned at about 20 degrees to about 30 degrees of retroversion. Once the cutting guide 160 is positioned in a selected position, it may be held in place with a fixation pin 326. It will be understood that more than one of the fixation pins 326 can be provided and pass through the bores 186, defined by the guide 160. The pins can include any appropriate type of pin and can be drilled into the humerus 310 to hold the cutting guide 160 relative thereto. The various other portions of the guide apparatus, including the guiding arm 172 and the fixation arm 170 can then removed from the reamer 20. In addition, the reamer 20 can be removed from the humerus to allow for a resection of the humeral head 310*a*.

The cutting guide 160 can be held in place with the pin 326 when all the other portions of the apparatus are removed. The saw 90 can then be used to resect the humeral head and the blade 200 can ride along a portion of the cutting guide 160. The cutting guide 160 can insure a proper orientation and/or position of the saw blade 200 relative to the humeral head 310*a*. Further, the glenoid shield 116 can be positioned relative to the glenoid 314 and other portions of the anatomy to assist in ensuring that the saw 200 does not engage portions of the anatomy not desired to be cut.

It will be also understood that the cut of the glenoid head 310*a* can be begun with the cutting guide 160 and then finished without the cutting guide 160. For example, an initial portion of the humeral head 310*a* can be resected with use of the cutting guide 160. After an initial portion of the cut is formed the cutting guide 160 and the fixation pins 326 can also be removed. The remainder of the cut of the humeral head 310*a* can then be performed using the initial portion of the cut formed with the saw blade 200 to guide the remaining portion of the cut. Therefore, it will be understood, that the cutting guide 160 need not be present to form the entire cut of the glenoid head 310*a*.

Osteophytes and soft tissue contractures can also be addressed. A one-half inch curved osteotomes (not shown) can be utilized to remove anterior, posterior, and inferior osteophytes from the proximal humerus 310. If the capsule is contracted anterior and posterior, it can be excised, and care can be taken not to disrupt the insertions of supraspinatus, infraspinatus, and subscapularis. The most common contracture, internal rotation contracture of the anterior capsule, can be easily visualized and resected without disrupting the overlying subscapularis muscle. Once the contracted capsule has been removed, the subscapularis may not need lengthening, as the muscle can stretch nicely, and is typically much more compliant than the retracted capsule which was excised. In an instance of significant tightness in the muscle itself, blunt dissection along the anterior neck of the glenoid with a Langenbach or Cobb retractor (not shown) can improve motion in an acceptable manner.

The glenoid condition can also be assessed, and a decision can be made for hemiarthroplasty or total shoulder arthroplasty. The glenoid is well visualized, and directly approached, as the surgical exposure is lateral as compared to other techniques. Glenoid version, glenoid erosions, and glenoid osteophytes are all easily assessed. Labral tissue is cleared from around the margins, and glenoid preparation can be carried out with a selection of straight reamers and drills. A keeled glenoid implant or pegged glenoid implant can be utilized, per the surgeons preference as discussed herein. Although the procedure can proceed according to any appropriate technique, glenoid preparation and implantation can occur prior to humeral broaching, but the humerus could be prepared first if desired.

Figure 14:
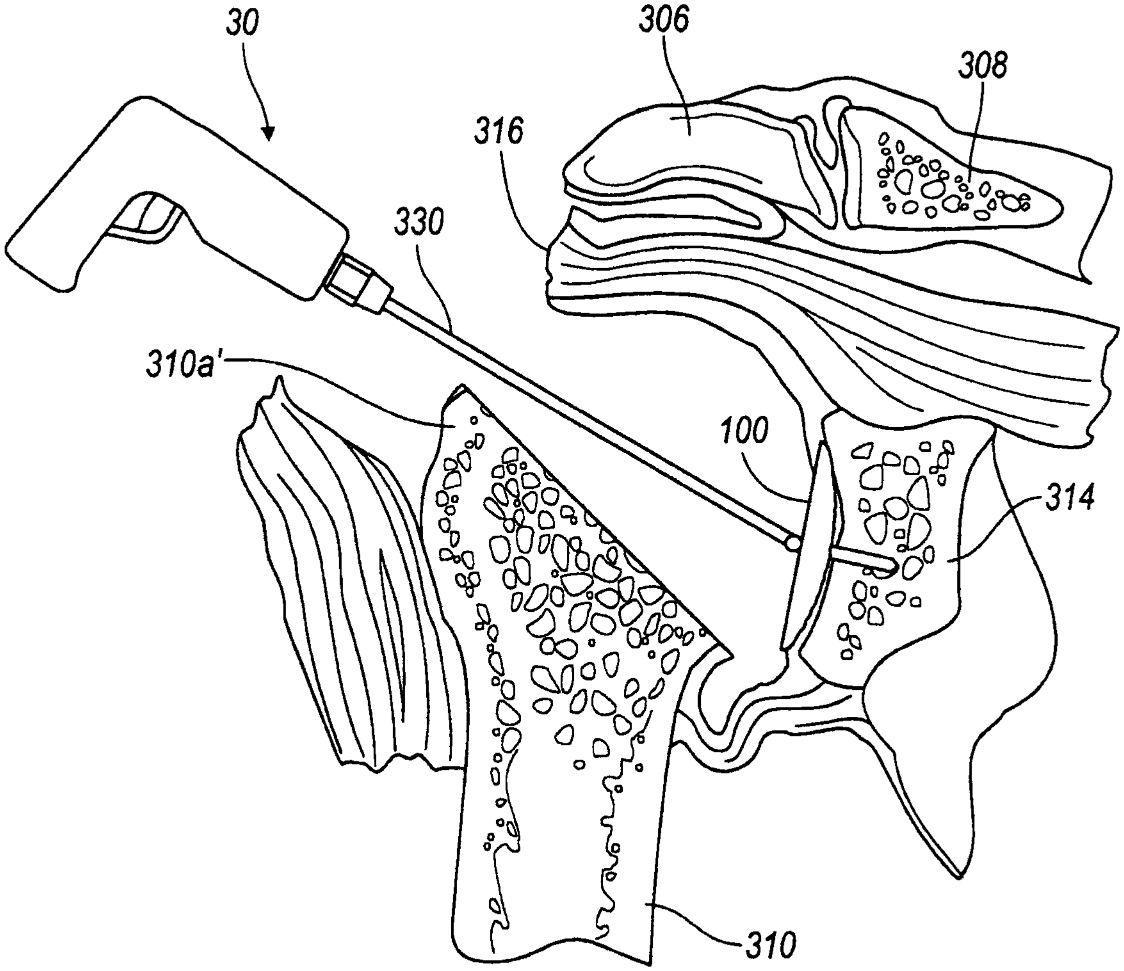
FIG. 14 is a detail cross-section view of an anatomy including an incision and positioning of various instruments according to various embodiments.

With reference to FIG. 14, once the humeral head 310*a* has been resected, thus forming the resected humeral head 310*a*', the glenoid 314 can be reamed with reamer 100. It will be understood that the glenoid 314 may be first prepared with the various procedures according to those commonly known in the art. Nevertheless, it will be understood that the various guides, such as those described herein, can be used to assist in achieving these procedures. For example, a glenoid sizer or central drill guide can be used for positions near the glenoid 314 to assist in forming a central drill bore or sizing the glenoid 314. As discussed above, various connecting portions can be positioned at a superior or top portion of the cisor or other instrument to assist in achieving the superior approach described herein. The reamer 100 can be interconnected with a reamer shaft 330 and a drill motor 30. This allows the reamer 100 to be rotated relative to the glenoid 314 to form the glenoid into a selected shape and orientation. The glenoid 314 may need to be shaped to allow for implantation of a selected glenoid implant. Nevertheless, it will be understood that the glenoid 314 need not necessarily be resected and may articulate with an implant positioned in the resected humerus 310.

Regardless, the reamer 100 can be positioned relative to the glenoid 314 and the shaft 313 extend through the incision 316 to allow for interconnection with the drill motor 30. After a selected period of reaming, the glenoid 314 can be prepared for implantation of a glenoid implant. As discussed above, the glenoid template 80 can be positioned relative to the reamed glenoid 314 to assist in further glenoid preparation.

Figure 15:
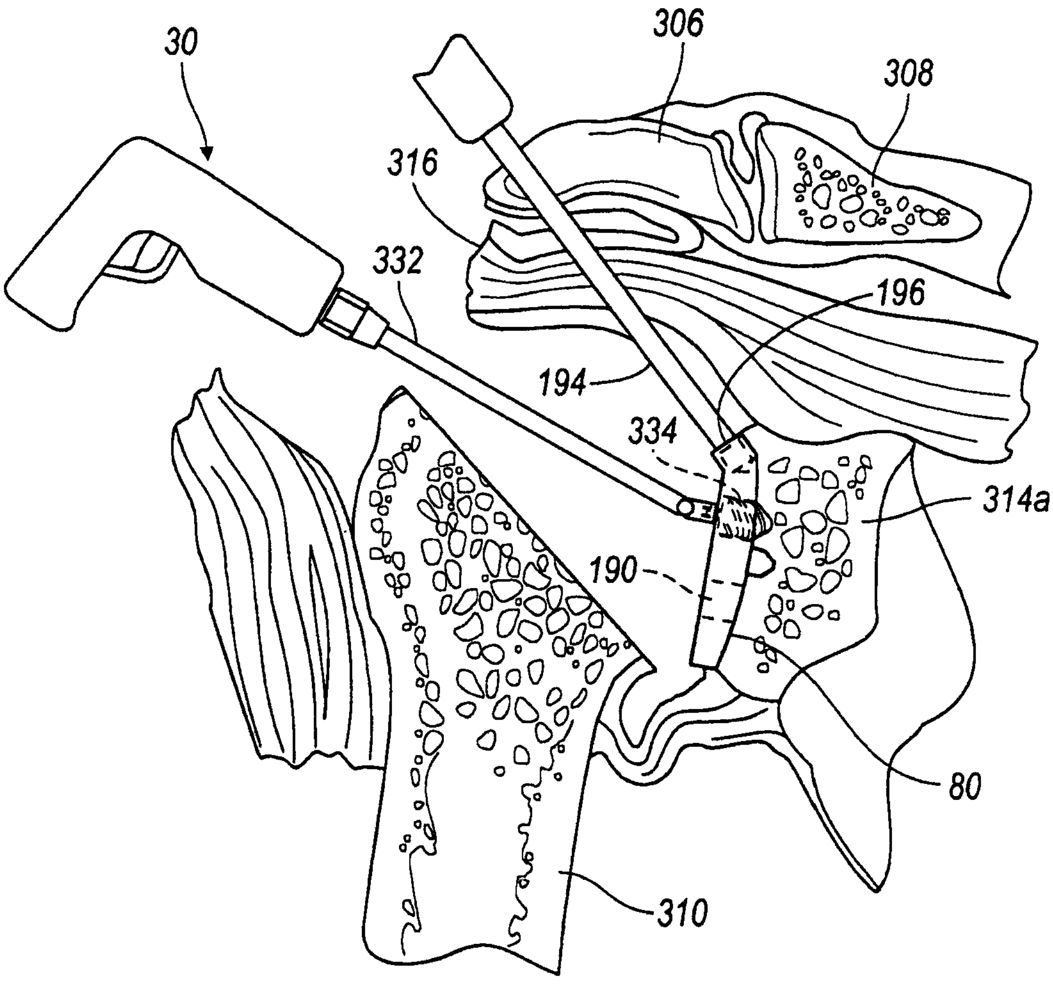
FIG. 15 is a detail cross-section view of an anatomy including an incision and positioning of various instruments according to various embodiments.
Figure 16:
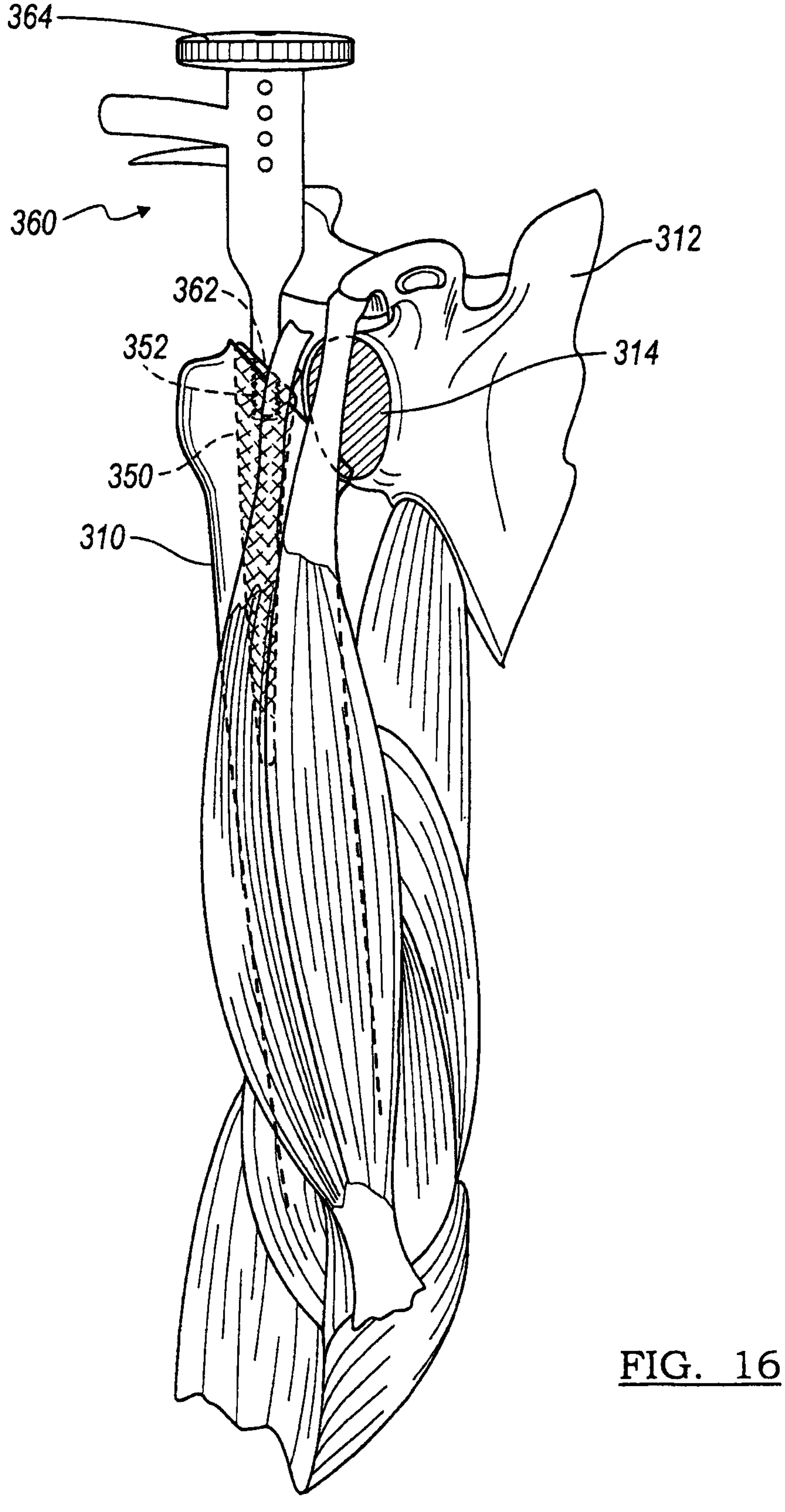
FIG. 16 is a detail cross-section view of an anatomy including an incision and positioning of various instruments according to various embodiments.

With reference to FIG. 15, the glenoid template 80 can be positioned relative to the reamed glenoid 314*a*. The shaft 194 that can interconnect with a connection region 196 and can extend through the incision 316 to allow access and manipulation by a user. The guide 80 allows for drilling or forming a plurality of bores in the resected glenoid 314*a* with a bit 334 that can be interconnected to the drill motor 30 with a shaft 332. The various bores formed in the resected glenoid 314*a* allow for interconnection and positioning of portions of a glenoid implant, such as pegs extending therefrom, into the glenoid 314. The pegs can be used to resist various motions of the glenoid implant, such as rotation, translation and the like. Further, the pegs allow for cementation points to cement the glenoid implant to the glenoid 314, if selected. Regardless, the guide 80 can be used relative to the glenoid 314 to form various bores, openings, and the like in the glenoid 314.

It will also be understood that other procedures generally known in the art may be used. For example, boring or drilling of inferior and superior holes can be formed in the glenoid 314 before the broach 130 is used. Nevertheless, these procedures are generally known and are not described here in detail. Further, the glenoid broach 130 can be used to form a keel opening in the glenoid 314, if selected. It may be selected to first form the bores in the glenoid 314, before attempting to form a keel opening. This may be selected for various reasons and may allow for a procedure to achieve a selected and superior result. Regardless, a glenoid implant may include one or both of a peg or a keel depending upon the selected glenoid implant.

Once the various bones of the anatomy have been resected, including the glenoid 314 and the humerus 310, the various implants can be implanted. Although the humerus 310 may need to be further prepared, such as broaching the IM canal of the humerus 310. Therefore, a broach may be provided and used to broach a selected portion of the IM canal of the humerus 310. Various sizes of broaches may be used to progressively enlarge the broached area of the humerus 310, as is generally known in the art.

A broach 350 can be formed in a plurality of sizes and include an attachment region 352. The attachment region 352 can interconnect with an inserter 360 and specifically a connection region 362 of the inserter 360. The inserter 360 can include an impaction head or portion 364 to allow for impacting the broach 350 into the humerus 310. The humerus 310 can be broached with increasing sized broaches. Also the humerus 310 can be trialed by interconnecting a humeral implant with a trial humeral head. This can first soft tissue laxity and resection accuracy.

The inserter 360 can also be used to implant a humeral implant 370. The broached IM canal in the humerus 310 can also be irrigated prior to inserting the humeral stem 372. The humeral implant 370 can also include a connection region 372 that is operable to interconnect with the connection portion 362 of the inserter 360. The humeral implant 370 further includes a head attachment portion 374 and a stem 376. The stem 376 is generally formed to fit into the broached portion of the humerus and further can be connected to the humerus with a selected cement or other portion. It will be understood, however, that the humeral implant 370 can include various bone ingrowth portions or other attachment regions to allow for interconnection of the humeral implant 370 with the humerus 310. Further, the humeral head implant 380 can be provided to interconnect with the humeral implant 370. The humeral head implant 380 can include a connection portion to interconnect with the humeral stem 370 to allow for the formation of a prosthetic humeral head.

It will be understood that although the humerus 310 can be implanted with a selected implant, including the humeral stem portion 370 and the humeral head 380, other appropriate implants can be positioned on the humerus 310 according to various embodiments of the presently described procedure. For example, a resurfacing implant that will replace an articulating portion of the humeral head can be positioned relative to the humerus 310 and the humeral head 310*a* using the above-described method.

Following implantation, the soft tissue balance can again be assessed, and then the split in the rotator interval can be closed. The deltoid can be repaired back to the acromion. Subcutaneous tissues and skin can then be closed per the surgeon's usual routine.

Further, a glenoid implant 390 including a keel 398 can be implanted in the glenoid. Alternatively, a glenoid implant 400 including at least a peg 402 can be implanted into the glenoid 314. Regardless, it will be understood that any appropriate glenoid implant including the glenoid implant 390, 400 can be positioned into the glenoid 314. The glenoid implants 390, 400 can be implanted with the glenoid positioner 194 that can be interconnected with the tool 50 to allow for positioning the glenoid 390, 400 relative to the glenoid 314.

Figure 17:
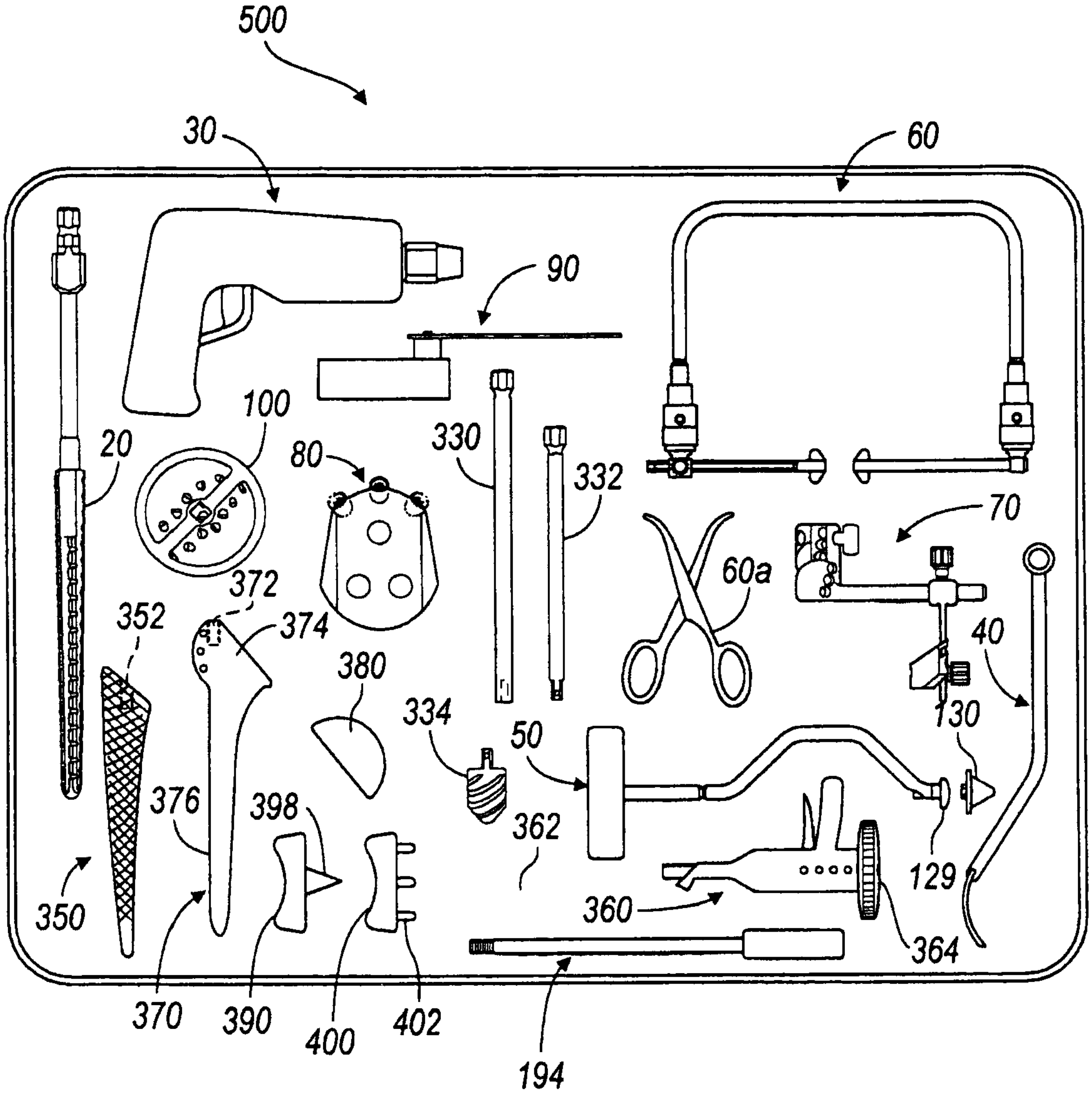
FIG. 17 is a kit of various instruments according to various embodiments.

Various portions described herein can be provided in a kit 500 as illustrated in FIG. 17. The kit 500 can include any appropriate portions that can be used in a selected procedure, such as a glenoid and/or humeral procedure and can include a plurality of the broaches 350, a plurality of the humeral implants 370, a plurality of humeral heads 380, a plurality of the glenoid implants 390, 400, and any other appropriate portion. Therefore, the kit 500 can be used for a plurality of procedures and need not be customized for a particular procedure or patient. Further, the kit 500 can include a plurality of portions that allow it to be used in several procedures for many differing anatomies, sizes, and the like. Further, various other portions, such as the reamer 100, the glenoid template 80, or other appropriate portions can be provided for a plurality of different patients.

Further, it will be understood that the procedure described above may be augmented slightly and still be within the scope of the teachings thereof. For example, an angled shaft may be used to interconnect the reamer 100 with the drill motor 30 to assist in moving the reamer 100 relative to the glenoid 314. The angled shaft may assist in positioning the drill motor 30 in an appropriate orientation relative to the glenoid 314 to achieve a selected resection. Further, the humerus 310 and the humeral head 310*a* can be repositioned by moving the humerus to assist in achieving access to the humeral head 310*a* or the glenoid 314. The arm positioning board 322 can further assist in holding the arm 301, and the bones therein, in a selected orientation to assist in performing the procedure. This can allow the user or the physician to achieve the procedure in the selected manner and further the movement of the arm 301, the arm board 322 or by an assistant, can assist in achieving access to the various portions of the anatomy without major dislocations of the various joints.

The description is merely exemplary in nature and, thus, variations that do not depart from the gist of the teachings are intended to be within the scope of the teachings. Such variations are not to be regarded as a departure from the spirit and scope of the teachings.

What is claimed is:

1. A humeral head resection guide, comprising:

a resection guide member defining a guide surface;

a first positioning member interconnected with said resection guide member;

a second positioning member interconnected with said first positioning member, said second positioning member including a rod attachment portion having a first plurality of version bores extending in a first direction, the rod attachment portion configured to receive a rod extending in a second direction transverse to the first direction, at least two of the first plurality of version bores defining a first line extending at an angle transverse to the second direction.

2. The humeral head resection guide of claim 1, wherein said resection guide member includes a length of about 2 centimeters to about 5 centimeters between a first end and a second end.

3. The humeral head resection guide of claim 2, wherein said guide surface extends substantially the length of the resection guide member.

4. The humeral head resection guide of claim 2, wherein the first positioning member defines a first track operable to interact with a first set screw to allow selected fixation of the resection guide member relative to said first positioning member.

5. The humeral head resection guide of claim 4, wherein said second positioning member defines a second track operable to interact with a second set screw to hold said first positioning member relative to said second positioning member.

6. The humeral head resection guide of claim 1, wherein said resection guide member is movable in at least three degrees of freedom.

7. The humeral head resection guide of claim 1, wherein said first positioning member allows for movement of the resection guide member in at least a first translation direction and a second translation direction and said second positioning member allows for a movement of the resection guide member in a third translation direction and a fourth translation direction and wherein said resection guide member is operable to rotate in a fourth or a fifth direction relative to said first positioning member or said second positioning member.

8. The humeral head resection guide of claim 1, wherein said guide surface is a slot defined by said resection guide member.

9. The humeral head resection guide of claim 1, wherein the first line extends at a first angle relative to the second direction, and wherein the rod attachment portion includes a second plurality of version bores defining a second line extending at a second angle relative to the second direction.

10. The humeral head resection guide of claim 9, wherein the first line is offset from the second line.

11. The humeral head resection guide of claim 4, wherein the first track includes a groove.

12. The humeral head resection guide of claim 8, wherein said slot extends from a first side of said resection guide member to a second side of said resection guide member, and wherein said resection guide member includes a plurality of throughbores extending from said first side to said second side.

13. The humeral head resection guide of claim 1, wherein said resection guide member is rotatably coupled to said first positioning member.

14. A humeral head resection guide, comprising:

a resection guide member defining a guide surface;

a first positioning member interconnected with said resection guide member; and a second positioning member interconnected with said first positioning member, said second positioning member including a rod attachment portion having a first plurality of version bores and a second plurality of version bores, the first plurality of version bores defining a first line extending in a first direction, the second plurality of version bores defining a second line extending in a second direction, the first line offset from the second line.

15. The humeral head resection guide of claim 14, wherein the rod attachment portion is configured to receive a rod extending in a third direction transverse to the first and second directions.

16. The humeral head resection guide of claim 14, wherein the first positioning member defines a first track operable to interact with a first set screw to allow selected fixation of the resection guide member relative to said first positioning member.

17. The humeral head resection guide of claim 16, wherein the first track includes a groove.

18. The humeral head resection guide of claim 14, wherein said resection guide member is movable in at least three degrees of freedom.

19. The humeral head resection guide of claim 14, wherein said resection guide member is rotatably coupled to said first positioning member.

20. A humeral head resection guide, comprising:

a resection guide member defining a guide surface extending along a cutting guide axis;

a first positioning member interconnected with said resection guide member;

a second positioning member interconnected with said first positioning member, said second positioning member including a rod attachment portion having a first plurality of version bores and a second plurality of version bores; and an orienting arm supported by the rod attachment portion and operable to be disposed within a humerus, wherein the first plurality of version bores are configured to secure the orienting arm in a first position relative to the cutting guide axis, such that the orienting arm and the cutting guide axis define a first angle therebetween, and the second plurality of version bores are configured to secure the orienting arm in a second position relative to the cutting guide axis, such that the orienting arm and the cutting guide axis define a second angle therebetween, the second angle being different than the first angle.

* * * * *